United States Patent [19]

Iwasaki

[11] 4,136,555

[45] Jan. 30, 1979

[54] REFERENCE-LOAD VARIABLE HARDNESS TESTER

[75] Inventor: Shozo Iwasaki, Ebina, Japan

[73] Assignee: Kabushiki Kaisha Akashi Seisakusho, Japan

[21] Appl. No.: 795,969

[22] Filed: May 11, 1977

[30] Foreign Application Priority Data

Jun. 28, 1976 [JP] Japan .................... 51-76181

[51] Int. Cl.² ............................................. G01N 3/44
[52] U.S. Cl. ...................................................... 73/83
[58] Field of Search ................................ 73/81, 83, 82

[56] References Cited

U.S. PATENT DOCUMENTS 2,667,065  1/1954  Ernst ........................................ 73/81
3,416,367  12/1968  Ernst ........................................ 73/81
3,939,700  2/1976  Anderson ................................. 73/83
4,023,401  5/1977  Ernst ........................................ 73/81

Primary Examiner—Anthony V. Ciarlante
Attorney, Agent, or Firm—Robert E. Burns; Emmanuel J. Lobato; Bruce L. Adams

[57] ABSTRACT

A reference-load variable hardness tester for measuring Rockwell hardness and Rockwell superficial hardness, having an internal coil spring and an external coil spring disposed coaxially with a load shaft for each reference-load. When measuring Rockwell hardness, both the internal coil spring and the external coil spring work for the reference-load, and when measuring Rockwell superficial hardness, only the internal coil spring works for the reference-load.

1 Claim, 1 Drawing Figure

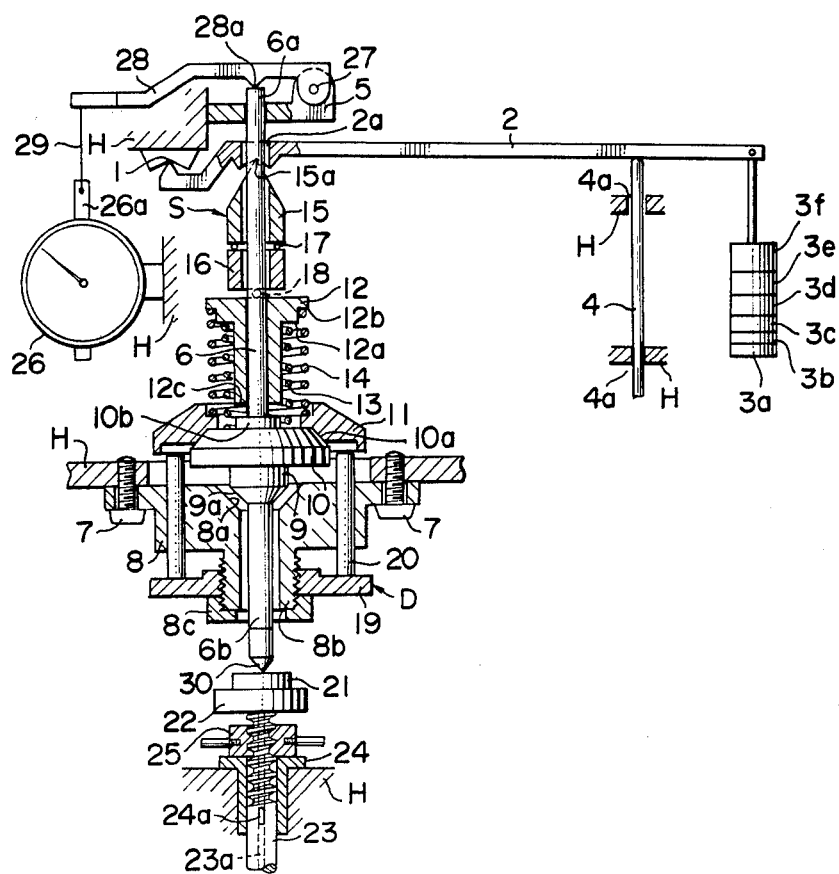

REFERENCE-LOAD VARIABLE HARDNESS TESTER

BACKGROUND OF THE INVENTION

This invention relates to a reference-load variable hardness tester that permits measuring two different types of hardness, such as the Rockwell hardness and the Rockwell superficial hardness, by changing the reference-load to be applied on the specimen.

In general, the Rockwell hardness test is practiced with the reference-load of 10 kgf, and the Rockwell superficial hardness 3kgf. Some conventional hardness testers have allowed the shifting between such reference-loads by changing the position of the weight on the load application mechanism, or by means of the remote-controlled load application system.

Despite its structural simplicity, the hardness tester with the shiftable weight requires much skill in its weight-shifting operation. Meanwhile, the remote-load-control hardness tester is complex and, therefore, very costly.

The object of this invention is to solve such problems of the conventional hardness testers. The more particular object of this invention is to provide a hardness tester that permits changing the reference-load with high accuracy, by simple operation, and without rendering the tester mechanism complex.

SUMMARY OF THE INVENTION

To attain this object, the reference-load variable hardness tester of this invention comprises a load shaft having an indenter at its lowest end, a receiving member fitted to the main body so as to support the flared portion of the load shaft from below, a stationary spring seat fixed to said shaft, an upper spring seat slidably fitted on said shaft, above said stationary seat, and adapted to receive a load applied by a load lever from above, coaxial internal and external coil springs for reference-load application compressedly interposed between said two spring seats, a movable spring seat detachably engaged on said stationary spring seat to receive the lower end of said external coil spring, and drive means to elevate the movable spring seat free of said stationary spring seat.

BRIEF DESCRIPTION OF THE DRAWINGS

Now a reference-load variable hardness tester, in which this invention is embodied, will be described by reference to the accompanying drawing, the single FIGURE of which shows a longitudinal cross section of the tester.

DESCRIPTION OF THE PREFERRED EMBODIMENT

From the main body or supporting and guiding frame H is extended a load lever 2 that is adapted to move about a fulcrum 1. This load lever 2 carries test load weights 3a, 3b, 3c, 3d, 3e and 3f at its extreme end. When test laod is not applied, the load lever 2 is supported by a control shaft 4 that moves up and down through a guide hole 4a in the main body or frame H.

The upper end 6a of the load shaft 6 passes through a guide hole 2a in the load lever 2 and a guide hole member 5 fixed to the main body or frame H. The lower end 6b of the load shaft 6 passes through a receiving member 8 attached to H with bolts 7. Being thus guided, the load shaft 6 moves up and down.

The load shaft 6 has a flared portion 9 outwardly extending therefrom, whose conical surface 9a is so designed as to fit the upper conical cavity 8a in the receiving member 8, but is normally spaced therefrom, as shown. A spring bottom seat 10 is fixed, stationary to the load shaft and shown at a lower position thereon, to extend outwards from on the flared portion 9. Further, above seat 10, a movable spring bottom seat 11 is detachably engaged on an upper conical surface 10a of the stationary spring bottom seat 10.

A cylindrical spring counter seat 12 is slidably fitted on the load shaft 6, above the spring bottom seats 11 and 10. An internal coil spring 13 for reference-load application is compressedly interposed between the internal spring receiving portion 12a of the counter seat 12 and the stationary spring bottom seat 10. Further, an external coil spring 14 for another reference-load application is compressedly interposed between an outer spring receiving portion 12b of the counter seat 12 and the movable spring bottom seat 11. The internal and external coil springs 13 and 14 are coaxial with the load shaft.

A load transmission member S is provided between the lower end of the guide hole 2a of the load lever 2 and the counter seat 12.

The load transmission member S consists of an upper transmission member 15 and a lower transmission member 16, both being generally cylindrical in shape and loosely fitted on the load shaft 6. The knife edge 15a formed at the upper end of the upper transmission member 15 is received by the knife edge seat formed at the lower end of the guide hole 2a.

Between the upper and lower transmission members 15 and 16 are horizontally provided a pair of load transmission balls 17 in a diametrical arrangement opposie one another at right angles with the knife edge 15a. Another pair of balls 18 are similarly interposed between the lower transmission member 16 and the upper spring seat 12, at right angles with the direction in which said pair of balls 17 are arranged. These balls 17 and 18 are contained in respective cavities not shown so as not to fall off.

A drive mechanism D to raise the movable spring bottom seat 11 off the stationary spring bottom seat 10 comprises a discoidal operating member 19 screwed on the externally threaded lower end 8b of the receiving member 8 and a plurality of (three, for instance) slide bars 20 adapted to be pushed up by said operating member 19. Each slide bar 20 passes through a vertical hole in the receiving member 8, so that the upper end of the slide bars 20, confronting the bottom surface of the movable spring seat 11, may push up this seat 11.

In order to prevent the operating member 19 from dropping, a stopper 8c is fixedly screwed on the lower end of the externally threaded end portion 8b of the receiving member 8. Further, suitable antifriction material is provided in the sliding area of the operating member 19 and the slide bars 20 that are pushed up thereby.

In the illustrated embodiment, the drive mechanism D is manually operated. But the operating member 19 may be motor-driven through a suitable gear mechanism, or a hydraulic jack may be attached to the slide bars 20.

A specimen 21 is placed on an anvil 22. A vertically moving shaft 23, perpendicularly fixed to the bottom surface of the anvil 22, is passed through a guide member 24 on the body or frame H and screwed into a rotating nut 25 on said guide member 24.

A key 24a protruding from the guide member 24 engages with a vertical key groove 23a formed along the axis of the vertically moving shaft 23, whereby the shaft 23 and the anvil 22 integrally move up and down as the nut 25 is rotated.

To the main body or frame H is fixed a dial gage 26 that indicates hardness on the basis of the downward displacement of the load shaft 6. A projection 28a on the lower side of a shifting lever 28, pivotally fitted to the guide hole member 5 with a pin 27, contacts the upper end 6a of the load shaft 6, with the farthest end of the lever 28 being connected to a spindle 26a of the dial gage 26 through a connecting rod 29.

To measure the Rockwell hardness of the specimen 21, the operating member 19 on the drive mechanism D is rotatingly lowered, to engage the movable spring bottom seat 11 with the stationary spring bottom seat 10, so that the forces of the compressed internal and external coil springs 13 and 14 are jointly applied on the load shaft 6. By elevating the shaft 23 by turning the nut 25, the specimen 21 is raised with the anvil 22 until the specimen 21 comes in contact with an indenter 30 at the lowest end of the load shaft 6.

When the specimen 21 is further raised, the conical surface 9a of the flared portion 9 of the load shaft 6 separates from the conical cavity 8a of the receiving member 8.

While thus leaving a suitable space between the lower end 12c of the upper spring seat 12 and the upper projection 10b of the stationary spring seat 10, the pointer on the dial gage 26 is set to the reference mark. At this time, a total of 10 kgf of load, including the loads of both coil springs 13 and 14, is applied on the specimen.

Then, by lowering the control shaft 4 supporting the load lever 2, the load lever 2 is turned about the fulcrum 1, whereupon the counter seat 12 is lowered through the upper transmission member 15, balls 17, lower transmission member 16 and balls 18 until its lower end 12c comes in contact with the upper projection 10b of the stationary spring seat 10. Namely, the test load is fully applied on the load shaft 6 on the detachment of the control shaft 4 from the load lever 2.

On returning the control shaft 4 to the original position, following the application of the test load, the test load is removed and only the reference-load of the coil springs 13 and 14 are applied on the load shaft 6.

In this state, the Rockwell hardness is read from the scale of the dial gage 26. The Rockwell hardness is determined in terms of the amounts of penetration of the indenter 30 into the specimen 21 before and after the application of the test load.

To determine the Rockwell superficial hardness, the reference-load to be applied on the specimen 21 is changed to 3 kgf by turning the operating member 19 of the drive mechanism D, whereupon the slide bars 20 push up the movable spring seat 11 off the stationary spring seat 10. As a consequence, the load of the external coil spring 14 is removed from the load shaft 6. After thus changing the reference load, the tester is operated in approximately the same procedures as for the measurement of the Rockwell hardness described before. Then, the Rockwell superficial hardness is read from the corresponding scale on the dial gage 26.

The weights 3a, 3b and 3c are used with the reference load of 3 kgf, for applying the test loads of 15, 30 and 45 kgf, respectively. Likewise, the weights 3d, 3e and 3f are used with the reference load of 10 kgf, for applying the test loads of 60, 100 and 150 kgf, respectively.

As will be understood from the above description, the reference-load variable hardness tester of this invention enables one to efficiently measure two different types of hardness, such as the Rockwell and Rockwell superficial hardness, with a single tester that requires only a simple reference-load shifting operation. The reference-load shifting can be accomplished easily; of the coaxially disposed internal and external coil springs, the latter may be disengaged from the stationary spring seat, which is integral with the load shaft, when the smaller load is required. Because of this structural simplicity, the hardness tester of this invention can assure ease of manufacture, availability at low cost, and accuracy of operation.

What is claimed is:

1. A variable reference load hardness tester, comprising;

a supporting and guide frame;

a load shaft movably supported by the frame, having an indenter at a first end and having, between the indenter and a second end, a flared portion of the shaft, outwardly extending therefrom;

a receiving member rigidly supported by the frame, surrounding the shaft adjacent the flared portion, having, remotely from the indenter, a relatively wide portion, and having, closer to the indenter, a relatively narrow portion, the wide portion having apertures extending along the shaft;

a spring and seat system for variable application of reference loads, comprising, a spring seat secured to the shaft to be stationary relative thereto, a counter-seat slidably fitted on the shaft opposite the stationary seat and having means for receiving a reference load from adjacent the second end of the shaft, an internal and an external coil spring, both coaxial with the shaft, for variable independent application of the reference load to the shaft, the internal spring being compressedly interposed between the stationary seat and the counter-seat, a movable spring seat engageable with the stationary spring seat and having means for receiving an end of the external coil spring for use of both coil springs in measuring one type of hardness;

drive means engageable with the apertures in the wide portion of the receiving member for returnably spacing the movable spring seat, guided by the apertures, from the stationary spring seat to returnably disengage it therefrom for use of the internal coil spring only in measuring another type of hardness; the drive means being directly, threadedly connected with the narrow portion of the receiving member, for thread-guided movement along the same;

the drive means comprising a discoidal operating member threadedly engageable with the narrow portion of the receiving member; and a plurality of slide bars secured to and upstanding from the operating member for sliding motion through the wide portion of the receiving member and for pushing engagement with the movable spring seat;

the receiving member having vertical holes receptive of the slide bars; and a stop screwed onto the narrow portion of the receiving member below the operating member to prevent the operating member from dropping and limit downward adjustment of said operating member.

* * * * *